US00PP24393P3

(12) United States Plant Patent
Danziger

(10) Patent No.: US PP24,393 P3
(45) Date of Patent: Apr. 15, 2014

(54) ***GAILLARDIA* PLANT NAMED 'DGAL7'**

(50) Latin Name: *Gaillardia pulchella*
Varietal Denomination: DGAL7

(75) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 93 days.

(21) Appl. No.: 13/506,748

(22) Filed: May 14, 2012

(65) Prior Publication Data

US 2013/0305423 P1 Nov. 14, 2013

(51) Int. Cl.
*A01H 5/00* (2006.01)

(52) U.S. Cl.
USPC ..... Plt./431

(58) Field of Classification Search
USPC ..... Plt./431
See application file for complete search history.

(56) References Cited

U.S. PATENT DOCUMENTS

PP15,966 P3 * 9/2005 Trees ..... Plt./226
PP16,649 P2 * 6/2006 Trees ..... Plt./431

* cited by examiner

*Primary Examiner* — Wendy C Haas
(74) *Attorney, Agent, or Firm* — Cassandra Bright

(57) ABSTRACT

A new and distinct *Gaillardia* cultivar named 'DGAL7' is disclosed, characterized by a well habit, unique bi-colored, red-purple and yellow-green flower, early blooming and long lasting and abundant flowering. The new variety begins blooming early in the season and flowers over a long period of time. The new variety is a *Gaillardia*, normally produced as an outdoor garden or container plant.

2 Drawing Sheets

Figure 1:
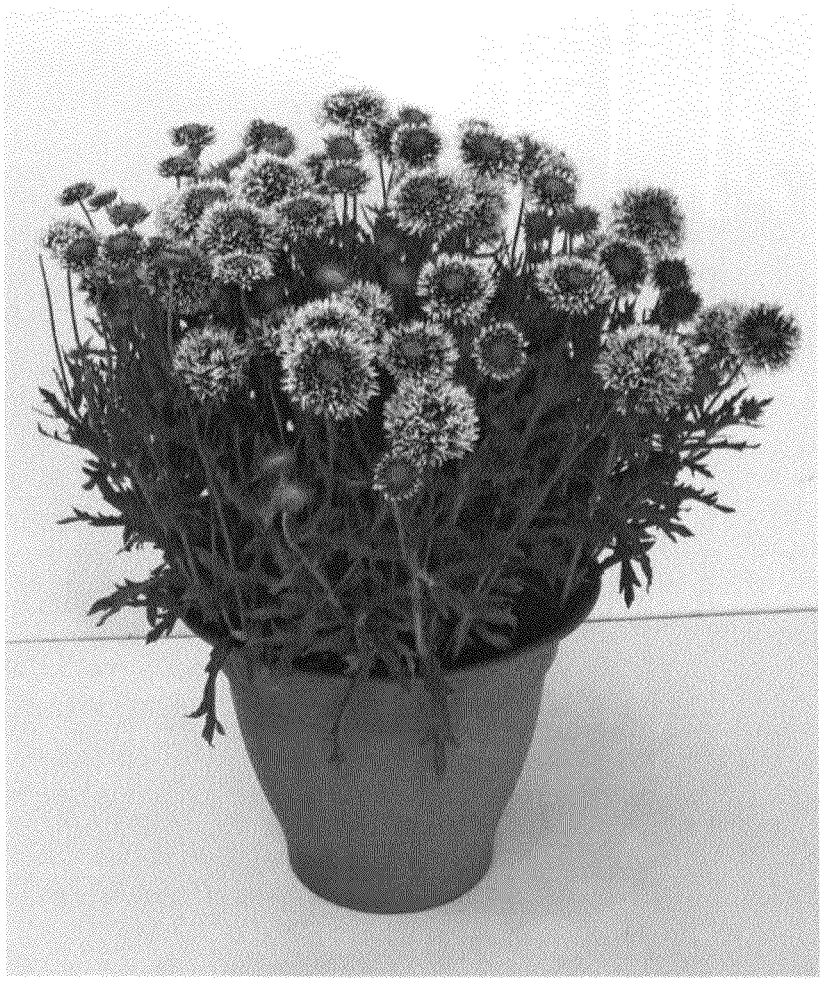

Latin name of the genus and species: *Gaillardia pulchella.* Variety denomination: 'DGAL7'.

BACKGROUND OF THE INVENTION

The new *Gaillardia* cultivar is a product of a planned breeding program conducted by the inventor, Gavriel Danziger, in Moshav Mishmar Hashiva, Israel. The objective of the breeding program was to produce new *Gaillardia* varieties for ornamental commercial applications. The cross resulting in this new variety was an open pollination made during August of 2007.

The seed parent is the unpatented, proprietary seedling variety referred to as *Gaillardia pulchella* 'GI-7-1102' The pollen parent is unknown, as the crossing resulting in 'DGAL7' was an open pollination, with unidentifiable pollen parents. The new variety was discovered in July 2008 by the inventor in a group of seedlings resulting from the 2007 crossing, in a research greenhouse in Moshav Mishmar Hashiva, Israel.

Asexual reproduction of the new cultivar 'DGAL7' by vegetative cuttings was first performed at a research greenhouse in Moshav Mishmar Hashiva, Israel in February 2009 and has shown that the unique features of this cultivar are stable and reproduced true to type in successive generations.

SUMMARY OF THE INVENTION

The cultivar 'DGAL7' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGAL7'

These characteristics in combination distinguish 'DGAL7' as a new and distinct *Gaillardia* cultivar:

1. Abundant flowering
2. Exceptionally long flowering season
3. Strong branching habit
4. Early blooming
5. Unique red-purple with green-yellow tipped flower color
6. Large flower Plants of the new cultivar 'DGAL7' are similar to plants of the seed parent, *Gaillardia pulchella* 'GI-7-1102' in most horticultural characteristics, however, plants of the new cultivar 'DGAL7' produce double flowers compared to the semi-double flower of 'GI-7-1102'. 'DGAL7' also produces a shorter plant with a more upright growth habit and less pubescent stems than 'GI-7-1102'.

COMMERCIAL COMPARISON

Plants of the new cultivar 'DGAL7' are comparable to the variety *Gaillardia* 'Torch Red Embers', U.S. plant Pat. No. 16,649 ('Baltoredem'), after reasonable research by the inventor. The two *Gaillardia* varieties are similar in most horticultural characteristics, however, the new variety 'DGAL7' differs in having more flowers and larger flowers than 'Torch Red Embers'. 'DGAL7' also flowers earlier, and has a flower that is bi-colored red-purple green-yellow tips whereas 'Torch Red Embers' has a red flower with yellow tip.

Plants of the new cultivar 'DGAL7' can also be compared to the commercial variety *Gaillardia* 'BALTORYEL' U.S. Plant Pat. No. 15,966. These varieties are similar in most horticultural characteristics, however 'DGAL7' has a bi-color flower, whereas 'Torch Yellow' has a solid yellow flower.

Additionally, 'DGAL7' has a more upright, firm plant habit and flowers earlier than 'Torch Yellow'.

BRIEF DESCRIPTION OF THE PHOTOGRAPHS

The accompanying photograph in FIG. 1 illustrates in full color a typical plant of 'DGAL7' grown in a greenhouse, in a 12 cm basket. Age of the plant photographed is approximately 8 weeks from a rooted cutting.

Figure 2:
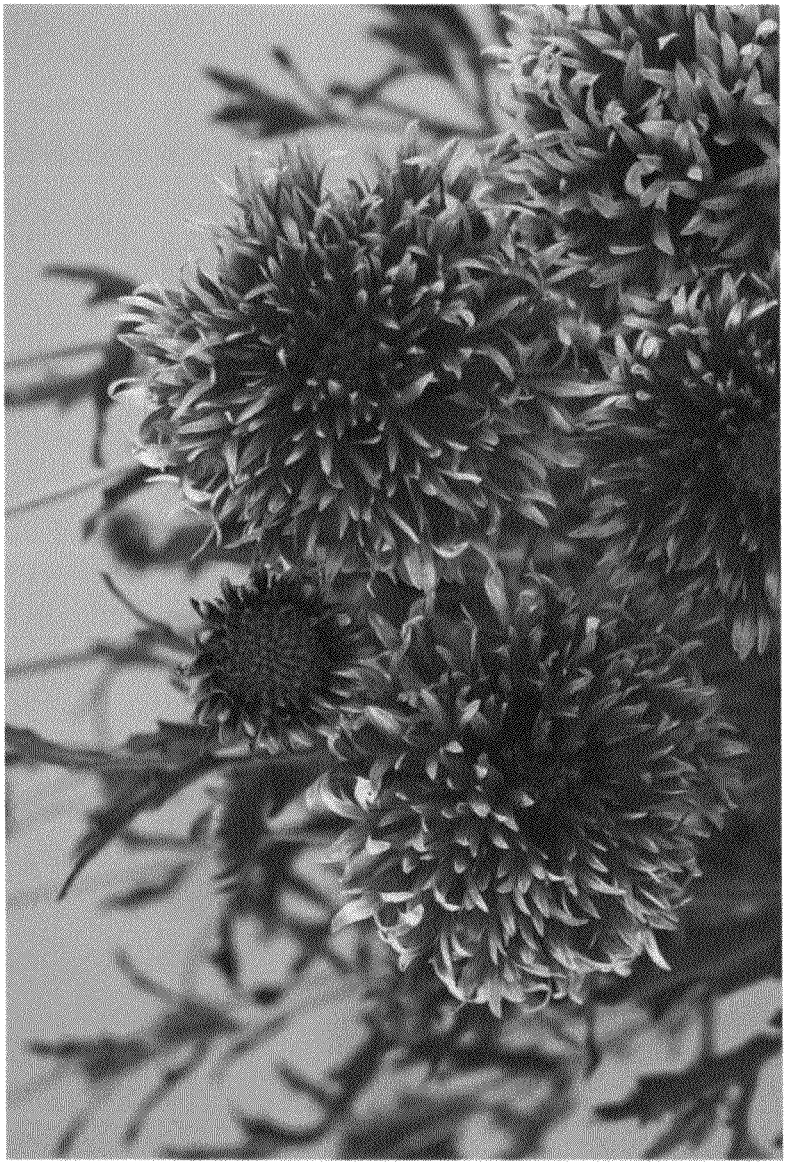

FIG. 2 illustrates in full color a close up of a typical bloom of 'DGAL7'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DGAL7' plants grown outdoors during Spring in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types. Plants are approximately 12 weeks old from a rooted cutting.

Botanical classification: *Gaillardia pulchella* 'DGAL7'.

PROPAGATION

Time to initiate roots: About 3-4 days summer, 4-5 days winter.

Root description: Fleshy, white, branching.

PLANT

Growth habit: Upright.

Pot size of plant described: 12 cm.

Height: 30-35 cm.

Plant spread: 30-40 cm.

Growth rate: Moderate.

Branching characteristics:

- *Length of primary lateral branches.*—15 cm.
- *Quantity of primary lateral branches.*—12.
- *Characteristics of primary lateral branches.*—Form: Basal Branching. Diameter: 0.7 cm. Color: RHS Yellow-Green Group 147D. Texture: Densely covered with short bristly hairs. Strength: Very strong.

Internodes length: 1.5-2 cm.

FOLIAGE

Leaf:

- *Shape.*—Pinnatifid.
- *Quantity.*—Approximately 50-70 per branch.
- *Average length.*—5 to 8 cm.
- *Average width.*—1.5 to 2.5 cm.
- *Apex.*—Acute.
- *Base.*—Wedge-shaped.
- *Margin.*—Lacerate.
- *Texture of top surface.*—Somewhat pubescent, not dense.
- *Texture of bottom surface.*—Somewhat pubescent, not dense.
- *Angle of attachment.*—45 degrees upwards.
- *Aspect.*—Mainly flat.
- *Color.*—Young foliage upper side: RHS Green 137A. Young foliage under side: RHS Green 137A. Mature foliage upper side: RHS Green 137B. Mature foliage under side: RHS Green 137B.
- *Venation.*—Type: Pinnate. Venation color upper side: RHS Green 138C. Venation color under side: RHS Green 138C.
- *Petiole.*—Absent.

FLOWER

Natural flowering season: March to August, throughout long day season.

Days to flowering from rooted cutting: 4 to 6 weeks.

Inflorescence and flower type and habit: Solitary, full flower.

Rate of flower opening: 3 to 5 days from bud to fully opened flower.

Flower longevity on plant: 5 to 7 days.

Persistent or self-cleaning: Self cleaning.

Flower size:

- *Diameter of entire flower.*—Approximately 6 cm.
- *Depth of flower.*—Approximately 3.5 cm.
- *Disc diameter.*—Disk florets absent — Fully double Flower.
- *Receptacle shape.*—Absent.
- *Quantity of inflorescences per lateral stem.*—3-5.
- *Quantity of open inflorescences and buds per plant.*—15-20.

Bud:

- *Shape.*—Flattened globular.
- *Length.*—0.5-1.0 cm.
- *Diameter.*—1.4-1.8 cm.
- *Color.*—RHS Yellow-Green 144B.

Ray florets:

- *Quantity.*—130.
- *Arrangement.*—Rotated in a triple whorl.
- *Length.*—2-3 cm.
- *Width.*—1.5-1.8 cm.
- *Shape.*—Trumpet-Shaped.
- *Apex.*—Looks like 5 separate but fused petals, acute.
- *Base.*—Fused into tubular shape.
- *Margin.*—Entire.
- *Texture, upper and lower surfaces.*—Smooth, Slightly ribbed longwise.
- *Color.*—When opening: RHS Red-Purple 60A (oblong part) and RHS Yellow-Green Group 154C at tips. Fully opened: RHS Red-Purple 59C (oblong part) and RHS Yellow-Green Group 154D at tips.

Disc florets: Disk Flores ABSENT, It's a Fully Double Flower.

Phyllaries/involucal bracts:

- *Quantity.*—45-50.
- *Length.*—1.5-2.5 cm.
- *Width.*—0.1-0.3 cm.
- *Shape (overall).*—Lanceolate.
- *Apex.*—Acute.
- *Base.*—Wedge-shaped.
- *Texture.*—Dull, Covered with short hairs.
- *Margin.*—Entire, with short hair directly on margin.
- *Color.*—RHS Yellow Green, Group 146A.

Peduncles:

*Length*.—Average 10-15 cm.

*Diameter*.—0.2 cm.

*Angle*.—About 45° to the lateral branch.

*Strength*.—Medium.

*Texture*.—Slightly glossy.

*Color*.—RHS Yellow Green Group 147B.

Fragrance: Slightly sweet scent.

REPRODUCTIVE ORGANS

Ray florets:

*Stamens*.—Number: 6.

*Anthers*.—Shape: Lance-shaped. Length: Approximately 0.2 cm. Color: RHS Red-Purple 60A. Pollen: Color: RHS Yellow-Orange Group 21A. Quantity: Medium amount.

*Pistil*.—Number: One present. Length: 10 mm. Style: Tubular. Length: 4 mm. Color: RHS Yellow group 6D.

Stigma: Shape: Bifid. Color: RHS Red-Purple 60A.

Ovary Color: RHS Yellow-Green Group 149B.

Disc florets: Disk Flores ABSENT, It's a Fully Double Flower.

OTHER CHARACTERISTICS

Seeds and fruits: 70-100 seeds per flower, Shape—oblong triangle, size—0.2 cm long×0.15 cm wide, with spiny crow on top 0.3 cm long×0.2 wide.

Disease/pest resistance: Neither resistance nor susceptibility to disease or pests has been observed in this variety.

Temperature tolerance: Upper temperature tolerance to at least 35° C. Lower tolerance unknown.

What is claimed is:

1. A new and distinct cultivar of *Gaillardia* plant named 'DGAL7' as herein illustrated and described.

* * * * *